United States Patent [19]

Black

[11] 4,014,743

[45] Mar. 29, 1977

[54] METHOD FOR CONTINUOUS PREPARATION OF COOKED THINNED STARCH PASTES

[75] Inventor: William C. Black, Cedar Rapids, Iowa

[73] Assignee: Penick & Ford, Limited, Cedar Rapids, Iowa

[22] Filed: Jan. 10, 1973

[21] Appl. No.: 322,362

[52] U.S. Cl. .............................. 195/31 R; 106/210; 195/115

[51] Int. Cl.² .......................................... C12D 13/02

[58] Field of Search .................... 195/31 R, 115, 25; 127/38, 32, 28, 71; 162/175; 106/210, 213, 150, 162

[56] References Cited

UNITED STATES PATENTS

| | | | |
|---|---|---|---|
| 3,133,836 | 5/1964 | Winfrey et al. | 127/32 X |
| 3,228,781 | 1/1966 | Halpert | 106/213 |
| 3,337,414 | 8/1967 | Wilson | 195/31 R |
| 3,371,018 | 2/1968 | Ewing et al. | 195/31 R |
| 3,450,549 | 6/1969 | Schwalbe | 127/32 X |
| 3,616,219 | 10/1971 | Massey | 195/31 R |
| 3,755,144 | 11/1973 | Ware et al. | 106/150 |

*Primary Examiner*—Raymond N. Jones
*Assistant Examiner*—Thomas G. Wiseman
*Attorney, Agent, or Firm*—Tilton, Fallon, Lungmus, Chestnut & Hill

[57] ABSTRACT

Method for continuous enzyme liquefaction of starch to produce cooked thinned starch pastes, in which an enzyme-containing suspension of raw starch is continuously added to an agitated body of heated converting starch in a single chamber tank, whereby the incoming starch is gelatinized and mixed with the partially converted material to maintain a blend within the tank, having a viscosity low enough to be readily agitated and pumped. A stream of the blend at an established pumpable viscosity is continuously removed from the conversion tank and treated to inactivate the enzyme. The process effectively eliminates problems resulting from the development of temporary peak viscosities in the usual enzyme liquefaction procedures, the equipment requirements are minimal, and the products as produced without further treatment are effective sizes and adhesives.

6 Claims, 1 Drawing Figure

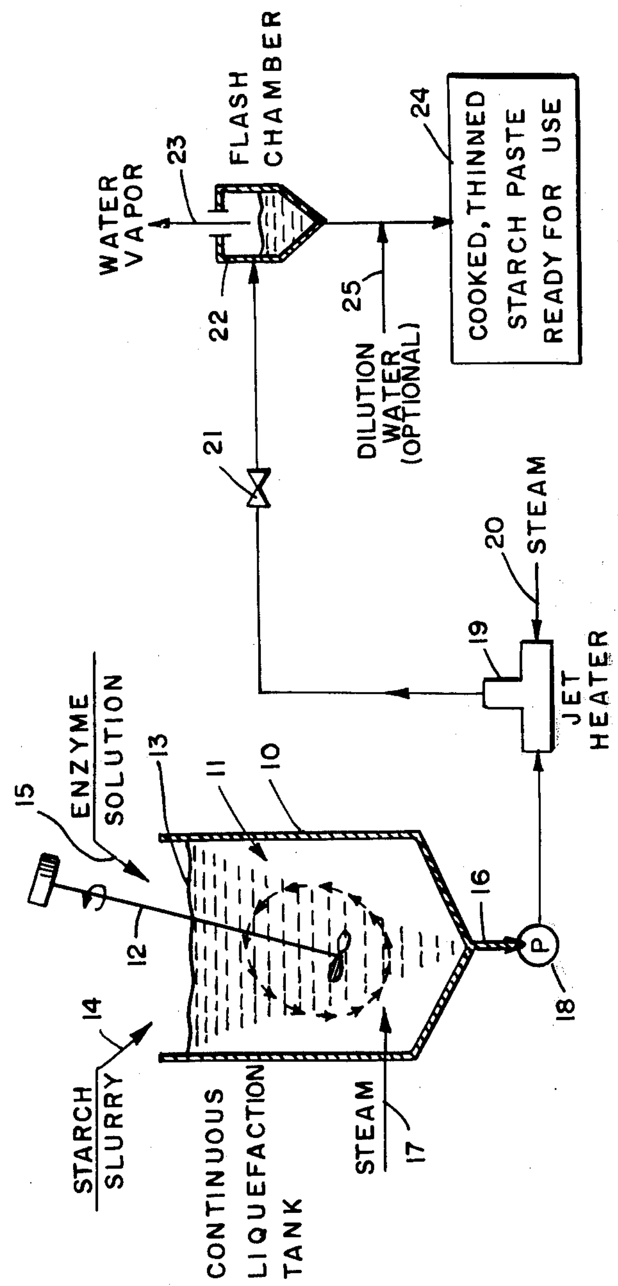
STARCH SLURRY
14
CONTINUOUS LIQUEFACTION TANK
STEAM
17
12
15
ENZYME SOLUTION
13
11
10
16
18
P
JET HEATER
19
20
STEAM
21
22
23
WATER VAPOR
FLASH CHAMBER
24
25
DILUTION WATER (OPTIONAL)
COOKED, THINNED STARCH PASTE READY FOR USE

METHOD FOR CONTINUOUS PREPARATION OF COOKED THINNED STARCH PASTES

BACKGROUND

In the paper and textile industries starch is widely used as a surface size for modifying the properties of yarns, fabrics and papers, and also as a binder for pigments in coated papers and filled textile fabrics. To be effective in such applications the starch must first be hydrated or gelatinized as by heating a water slurry or suspension. If unmodified or native starch is used, the resulting paste viscosity is frequently too high to permit the preparation of a paste of the desired concentration so some sort of starch depolymerization treatment is necessary to enable the desired concentration-viscosity relationship to be obtained. Starch depolymerizing enzymes, such as alpha amylase, are commonly used for this purpose.

When a slurry or water suspension of starch granules is heated, the granules start to swell at the so-called gelatinization temperature and progressively swell further as the temperature is increased. Increases in both the number of swollen granules and in their individual size causes an increase in the viscosity of the paste so that it increases rapidly as cooking proceeds, at least in the initial stages of the cooking process. However, the swollen granules are fragile and tend to fragment under the influence of shear in the cooking vessel so that their individual contribution to the viscosity of the paste is lessened. As a consequence of these two effects, the paste viscosity increases rapidly initially and then at a slower rate as the effect of fragmentation becomes apparent. Where the increase due to additional granule swelling is just balanced by the viscosity lowering due to granule fragmentation, a peak viscosity is obtained. Beyond this point, the effect of the fragmentation becomes predominant and on continued cooking the paste viscosity decreases and eventually stabilizes when both additional swelling and fragmentation become negligible.

In the conventional enzyme depolymerization, the enzyme, usually a bacterial alpha-amylase, is added to the starch slurry along with enzyme stabilizers and pH adjusting agents and the batch is put through a temperature cycle during which the starch is simultaneously gelatinized and depolymerized. When the desired conversion is attained, the temperature of the paste is raised to a level near the boiling point to complete the hydration of the starch and to inactivate the enzyme. While the viscosity vs. time curve for such a conversion varies somewhat from that of a cook of the starch alone, it normally evidences a considerable peak viscosity followed by a viscosity drop similar to that of the starch cook. Especially at higher starch concentrations, such enzyme conversions frequently exhibit high peak viscosities which may limit the concentration of the pastes which can be prepared or which may make necessary the use of heavy and expensive mixing equipment with an accompanying high power input. A variety of systems have been proposed for continuously cooking and enzyme-converting a stream of starch but here also the peak viscosity evidenced by the paste has been troublesome (and often limiting) and has made necessary the use of heavy agitators, scrapers, pumps, etc.

Heretofore, it has been believed that to be effective as a size or adhesive, the starch granules contained therein should all be hydrated and converted to the same degree; and that it was, therefore, necessary that they all be subjected to the same cooking and converting conditions (time-temperature cycle). This, of course, is automatically accomplished in an agitated batch-type conversion or cook. (See, for example, U.S. Pat. No. 3,450,549.)

In continuous conversion systems, such a uniform treatment for each granule is obtained or approached by the use of a relatively long, narrow cooking or hold chamber where the resulting so-called "plug flow" therein results in a reasonably uniform exposure of all of the starch granules to the same conditions as they pass through the chamber. In such a device, the high peak viscosity attained by the paste in the early stages of treatment may make necessary the use of heavy agitators, scrapers, etc., to minimize channelling and dead spots as the starch proceeds through the chamber.

Starch conversion using a plug-flow type reactor column is described in U.S. Pat. No. 3,371,018. A vertical reactor column was equipped with horizontal baffles and with a rotating shaft in the center. As described in the patent, the action was as follows: "The shaft is loaded with flow-directing blades and turbines which impart an internal flow pattern in the column so that the mass has a forward turbulent flow with the minimum of back-mixing. A positive displacement pump forces the slurry into the column and gives the forward flow." Paper mill tests using similar equipment were described in a paper presented by Cave and Adams at a Tappi coating conference in 1968. The mixture of water, starch, enzymes, was pumped into the top of a vertical reactor having a mixer for uniformly applying the feed across a distributor plate. No agitation was provided in the long central section of the reactor where a completely plug-type flow was obtained. From these and similar prior art disclosures, it was known, therefore, that plug-type flow continuous reactors produced enzyme converted starch pastes suitable for use as paper sizes or coatings.

Another procedure which contributes to the uniform exposure of each granule to the same conditions is the use of multiple conversion tanks arranged in series where a step-wise level of conversion is obtained as the product flows from tank to tank. In this instance, also, the peak paste viscosity in the early stages of conversion frequently requires the use of heavy agitation equipment, etc., or limits the concentrations which can be effectively handled.

SUMMARY

A new procedure has now been discovered for continuously enzyme-converting a starch paste, which effectively eliminates the problems associated with the development of apeak viscosity, and so minimizes the equipment requirements. At the same time it produces a product which is a mixture of highly converted and lesser converted starch, which is effective as a paper and textile size, as a paper coating binder, etc. A unique feature of the process is that instead of attempting to gelatinize and convert each granule of starch uniformly, in which case the simultaneous swelling of the granules creates a troublesome peak viscosity, a non-uniform conversion is intentionally effected. This is accomplished by the continuous addition of a feed stream of raw starch slurry and necessary enzyme to an agitated and continuously back-mixed body of starch, which has already been gelatinized and partially converted by the continuous enzyme treatment. In a preferred procedure, the agitated body of partially converted starch is maintained at such a temperature that an enzyme conversion is in progress and that the raw starch in the incoming feed stream is gelatinized when it contacts and is mixed with the agitated body of partially converted material. Instead of the viscosity of the starch suspension increasing to a peak viscosity because of the addition of the raw starch, the body of starch in the continuous liquefaction tank can be maintained at a pedetermined selected viscosity at which it can be readily stirred and pumped, thereby permitting the continuous removal of the blend of starch granules which have been subjected to differing degrees of enzyme conversion.

THE DRAWING

The method of this invention is illustrated schematically in the accompanying flow sheet, which will be subsequently described.

DETAILED DESCRIPTION

The method of this invention is adapted for the continuous preparation of cooked thinned starch paste ready for application, such as for sizing or coating paper or use as an adhesive. In practicing the method, a water slurry of raw granule starch is continuously introduced into a tank providing a single chamber converting zone. This converting zone is equipped with agitation means. There is also continuously introduced into the converting zone a water solution of starch thinning enzyme. The introduction of the feed comprising the starch slurry and the enzyme reagent, which may be introduced separately or together, is controlled in relation to the removal of the starch paste product from the zone so that there is maintained in the converting zone a continuously agitated and substantially uniformly mixed body of suspended starch. The temperature of this body is controlled to maintain the body at a temperature sufficient to gelatinize the incoming raw starch and suitable for the action of the thinning enzyme on the gelatinized starch, thereby the starch is liquefied and its viscosity is reduced by enzyme conversion. The resulting product is non-uniform with respect to molecular size or chain length of the starch, and consists of a blend of starches which have been subjected to different degrees of enzyme conversion. This is due to the fact that the heating and enzyme treatment of the raw starch is non-uniform for the individual starch granules or molecules. The resulting blend, comprising the product of cooked thinned starch paste, is continuously withdrawn from the converting zone in proportion to the volume of the feed. The average residence time of the withdrawn blend within the converting zone is controlled to achieve the desired viscosity reduction without appreciable production of reducing sugars. In steady state continuous operation, the blend within the converting zone does not go through a viscosity cycle but rather maintains a selected predetermined maximum viscosity, which is the desired viscosity of the liquefied product. The withdrawn liquefied product is not held for further enzyme conversion but rather is subjected to enzyme inactivation. Thus the enzyme thinning action is terminated without substantial further enzyme conversion of the blend. The enzyme inactivated starch paste is therefore ready for use although it still contains a wide distribution of different molecular size material. Contrary to the teachings of the prior art, however, as will subsequently be shown, such pastes are as effective for use as sizes, coatings, or adhesives as starch which has been uniformly converted, either in a batch-type conversion, or in a plug-flow type reactor.

The method of the present invention can be practiced in very simple and relatively inexpensive equipment, while at the same time producing a cooked thin starch of predetermined characteristics ready for immediate use. For example, as illustrated by the accompanying flow sheet, a continuous liquefaction tank 10 can be utilized to provide an open, single chamber converting zone 10. No interior baffles or compartments are required, thus keeping the cost of tank 10 to a minimum. The tank is provided with agitation means, such as the motor-driven agitator-impeller 12. As indicated, the body of converting starch 13 is maintained within tank 10 under continuous agitation. The amount of agitation should be sufficient to maintain the body of starch as a substantially uniform mixture, even though a feed starch slurry and an enzyme solution feed is being continuously supplied, as indicated at 14 and 15. It will be understood, of course, that in the immediate vicinity of the addition of the feed, such as at the top of the body 13, some non-uniformity is inevitable. However, the incoming feed can be quickly mixed into the distributed throughout the starch body 13, so that the body as a whole comprises a substantially uniform mixture. It should be emphasized that all portions of the starch suspension within tank 10 are maintained in agitation, including the starch suspension in the lower portion of tank 10 adjacent the outlet 16 from which the converted product is withdrawn on a continuous basis. This means that there is no plug-type flow within the converting zone 11, but rather there is continual back mixing from the lower to the upper portion of the tank, thereby maintaining a substantially uniform mixture, as previously described.

Starch product withdrawn through outlet 16 is therefore identical to the body of starch within converting zone 11. It comprises a blend of starch of differing degrees of enzyme conversion. On an individual granule or molecular basis, the residence time will vary greatly, although the feed and product streams are proportioned to maintain a uniform volume body within tank 10.

To promote the gelatinization and enzyme conversion of the starch, tank 10 is provided with heating means for applying controlled heat to the body of starch therein. For example, as indicated at 17 live steam may be directly introduced into the body of starch, the amount introduced being controlled to maintain a pre-determined temperature. Alternatively, tank 10 can be jacketed for circulation of a heating fluid therearound to provide indirect heating of the starch within the tank. Direct steam injection is desirable since the steam can provide further agitation for the starch suspension.

The viscosity of the withdrawn starch will be such that it can be pumped. As indicated at 18, a pump can transfer the stream of withdrawn starch paste to a jet heater 19 for deactivation of the enzyme in the paste. Within heater 19, the withdrawn paste is brought into contact with steam, as indicated at 20, and the paste is heated to a temperature above that at which the enzyme is stable, resulting in complete inactivation of the enzyme. Where the jet heater 19 is operated under super-atmospheric pressure, as will normally be preferred, the paste after enzyme inactivation can be passed through a back pressure valve 21 to a flash chamber 22 for removal of water vapor as indicated as 23. The flash chamber being operated at atmospheric pressure, will reduce the temperature of the starch paste to approximately 212° F. The starch paste, either with or without further cooling, is ready for use, and may be continuously suppled to a point of use, or it can be temporarily stored, as indicated at 24. It will be understood that diluting water may be added as indicated at 25. The cooked, thinned starch paste is then ready for use.

While the use of a jet heater for inactivation of the enzyme is convenient, and may also be used to practice the process of U.S. Pat. No. 3,133,836, it is not essential. Alternatively, the enzyme in the cooked thinned paste from converting tank 10 may be inactivated by chemical means (e.g. lowering the pH), as is well known in the enzyme treatment art, or by otherwise heating the paste to an enzyme inactivation temperature. This may be done by a batch procedure or by the use of scraped-film, or other suitable indirect heat exchanges. Whatever inactivation procedure is used, it is preferred to accomplish this before any substantial further conversion of the starch has occurred. By passing the withdrawn stream from tank 10 directly to a jet heater, the enzyme can be inactivated almost immediately after withdrawal of the paste. If further viscosity reduction of the paste product is desired, or more complete fragmentation of the swollen granules is desired, excess steam can be used in the jet heater, that is, more steam is introduced to the heater than that required to heat the starch paste to the enzyme inactivation temperature. This method is more fully described in U.S. Pat. No. 3,133,836. While the excess steam treatment of this patent can be used in conjunction with the non-uniform enzyme conversion of this application, the combination is optional, although it may be preferred in certain embodiments, as indicated above.

For the most advantageous practice of the method of the present invention, certain process conditions can be followed. The starch slurry, comprising the feed of raw starch to the conversion zone, will usually have a starch concentration within the range from 10 to 45% by weight on a dry solids basis. Even where starch pastes are desired of concentrations of less than 10%, such as a concentration of 5%, it will usually be more advantageous to convert the starch at a higher concentration, such as at a concentration above 15%, such as 20 to 40% on a dry solids basis, and then dilute the converted starch to the desired use concentration. Such high solids liquefaction is feasible because the method avoids a peak viscosity as the incoming raw starch gelatinizes. In the preferred method of operation, the blend within the liquefaction tank is maintained at a predetermined selected viscosity well below a viscosity which would interfere with stirring or pumping of the blend. The blend is also continuously removed at the selected predetermined viscosity. In general, the process will be controlled to limit the maximum viscosity of the blend within the tank to not over 5000 centipoises, as determined by Brookfield Viscometer, the test being made at 100 rpm and 190° F.

The process can be utilized with all types of raw starches which are applied as cooked starch pastes. Such starches include particularly corn starch and potato starch. To prepare the slurry for feeding to the conversion zone, dry granule starch can be suspended in water. Precooked or pregelatinized starches may be treated by the process but such a treatment is usually not advantageous. The starch, which preferably is in its uncooked or raw state, may be in its native or unmodified condition, or it may have been previously modified as with mild acid or oxidizing agents or with derivatizing agents.

The enzyme used for the conversion is preferably a bacterial alpha amylase which is stable and active at a temperature above the gelatinization range of the starch. To protect the enzyme (as is well known in the enzyme treatment art), calcium ions ($Ca^{++}$) may be incorporated and the pH of the starch slurry may be adjusted with suitable buffering salts to maintain the optimum conditions for enzyme stability and activity. It is optional whether the calcium ion providing reagent, and the pH adjusting agent are premixed with the starch slurry, although this is convenient. Also, if desired, the water solution of the enzyme may be premixed with the starch slurry, but it may be more convenient to meter the enzyme solution separately from the starch slurry.

As the viscosity lowering effect of the enzyme is a function of the time the starch remains in the conversion tank, the viscosity of the final product decreases as the average hold up time in the conversion tank is increased and also as the amount of enzyme used in increased. It is, therefore, necessary to select the enzyme level which will effect the desired depolymerization (viscosity-lowering) with the hold time being used. The latter, of course, is dependent upon the size of the conversion tank as well as the rate of flow of the product through the system. By varying the flow rate, conversion tank size, and enzyme level a wide range of product viscosities (at a given concentration) may be obtained, and, also, a product having a desired final viscosity and concentration can be obtained using many different combinations of these same three factors. The tank size selected as well as the flow rate used will depend upon the needs of the user as well as on the size and cost of the equipment available and on the enzyme unit cost, etc. The hold time may be from a few minutes to a few hours and the enzyme level used must be adjusted accordingly to produce a product of the desired viscosity.

Having in mind the foregoing general principles, the desirable range of enzyme concentration, conversion temperatures, and hold or residence times within the converting tank can be illustrated.

For example, bacterial alpha amylase having an activity of 35,000 to 850,000 MWU/pound dry weight of starch can be employed. For products designed for paper surface sizes the enzyme concentration will usually range from 35,000 to 150,000 MWU/lb. of starch and for high solids paper coatings will be in the 200,000 to 400,000 MWU/lb. of starch range. For producing a product for any given use, of course, the necessary enzyme level may vary considerably depending upon the hold or reaction time as well as on the other conditions that prevail during the process. (The potency in MWU refers to Modified Wohlgemuth Units as determined by Assay Method No. 2-124 of the Miles Chemical Co., Elkhart, Ind.)

The temperature of the body of starch during conversion should be such that the entering starch rapidly gelatinizes and the temperature should favor the enzyme conversion. For commercially available heat-resistant bacterial alpha amylases, suitable temperatures will be in the range from 170° to 210° F., with the optimum temperature usually being within the range from 180° to 200° F. For maximum enzyme activation a pH of 6.5 to 7.0 is desirable. The average residence time of the withdrawn paste product will usually fall within the range from 5 to 60 minutes, although in some applications, a shorter or longer hold time can be employed. For substantial viscosity reduction with the indicated enzyme concentrations, hold times of at least 10 minutes, such as 15 minutes or more, may be used. The extent of conversion thus obtained does not produce an appreciable amount of reducing sugars. Even with the maximum enzyme concentrations, conversion temperatures, and hold times, the reducing sugar content of the product will usually be less than 3% on a D.E. (Dextrose Equivalent) basis.

The process is further described in the following examples which are intended to be illustrative rather than limiting.

EXAMPLE I

A 20.3% (D.S.) concentration slurry of unmodified raw corn starch was prepared and adjusted to pH = 7.0 with $Ca(OH)_2$. A bacterial alpha amylase enzyme (HT-1000 of Miles Laboratories — alpha amylase activity = 745,000 MWU/fm) was then added in an amount equal to 0.05% of the dry starch weight. The potency designation MWU designates Modified Wohlgemuth Units, as determined by Assay Method No. 2-124 of the Miles Chemical Co., Elkhart, Indiana. On a weight basis, enzymes of comparable potency to HT-1000 can be used within the range of 0.01 to 0.25% based on the dry weight of the starch. 25 gallons of water were run into the conversion tank and heated by steam injection to 195° F. at which point a slurry pump was started to pump the slurry to the conversion tank at the rate of 1.5 gal./min. The conversion tank which was like that illustrated in the flowsheet drawing, was maintained at 195° F. by automatically controlled steam injection and when the contents amounted to 45 gallons, a transfer pump was started and adjusted to the speed necessary to maintain the tank contents at a uniform level. The average residence time thus obtained was about 30 minutes. The effluent from the conversion tank was mixed with steam in a jet mixer-heater and the steam flow and back-pressure valve was adjusted so that the temperature was raised to 320° F. and the steam flow was 3.5 times the quantity which would have been required to raise the temperature to 320° F. if it had all been condensed. The quantity of steam is not critical and can be reduced to the theoretical amount required to raise the temperature to 320° F. The cooked paste was flashed to atmospheric pressure and tested, as shown below in Table A, with the time noted being that elapsed since the initial starch slurry flow was started.

Table A

| Elapsed Time (min.) | % Solids (refractometer) | Viscosity-150° F. Brookfield Viscosity (cp.) | Viscosity-150° F. Dudley Viscosity (seconds) | Reducing Sugars (% as dextrose) |
|---|---|---|---|---|
| 50 | 15.0 | 32.0 | 56.9 | 0.9 |
| 65 | 16.0 | 35.5 | 58.8 | — |
| 90 | 16.5 | 35.0 | 57.7 | 1.0 |
| 115 | 17.0 | 32.5 | 57.3 | — |
| 130 | 17.5 | 34.5 | 57.1 | 1.0 |

The concentration of the initial converted product was low due to the use of the water heel in the reaction tank at the start of the cook. This is only a start-up condition. The above data on samples taken after the concentration had stabilized indicates the process is effective in producing a product with a reduced and uniform viscosity.

One of the reasons that has been advanced for using procedures directed to producing a uniformly converted product is that such procedures result in a lower formation of reducing sugars which are believed to have minimal adhesive value. The above data indicates that the subject process does not produce reducing sugars in excess of those produced by conventional enzyme conversion procedures.

EXAMPLE II

The process of Example I was repeated using a 40% D.S. unmodified raw corn starch slurry to which had been added calcium hydroxide equivalent to 0.04% calcium ions on dry starch. The slurry was adjusted to pH = 7.0 and a bacterial alpha amylase enzyme (HT-1000 of Miles Laboratories) equal to 0.12% of the dry starch weight was added. The flow rate and converting tank contents were maintained so that the average tank holdup or residence time was 10 minutes. During the run, the viscosity of the converting tank contents having approximately 40% solids concentration was readily agitated as its viscosity remained in the 3000–4000 cp. range at 195° F. The converting tank effluent was pressure cooked as before and the effluent from the flash chamber was continuously diluted with 110° F. water to give a final solids of 17.5%.

For comparison, a corn starch slurry of 17.5% solids was converted with a bacterial alpha amylase enzyme by a conventional batch conversion process consisting of a 20 minute hole period at 170° F. followed by 10 minutes at 205° F. The data is summarized in Table B.

Table B

| Elapsed Time (min.) | % Solids (Refractometer) | Viscosity - 150° F. cp. (Brookfield) | Viscosity - 150° F. Dudley (seconds) | Reducing Sugars % |
|---|---|---|---|---|
| 48 | 17.5 | 30.5 | 45.5 | — |
| 68 | 17.5 | 29.5 | 44.6 | 1.7 |
| Conventional Batch Conv. | 17.5 | — | 46.5 | 2.0 |

The above data illustrates that at comparable levels of starch conversion the reducing sugars produced by the subject process are no more than is produced by a conventional batch enzyme conversion. It is apparent, also by comparison with Example I, that the process is effective for pastes having a wide range of starch concentrations, these showing the use of 10 – 40% D.S. slurries.

EXAMPLE III

The products of Example II were heated to 150° F. and applied to the surface of an unsized, 30 lb., bleached fiber, free, offset sheet using a Keegan laboratory size press operating at a speed of 70 fpm. The sized sheets were conditioned and checked for size pick-up, burst strength, porosity and wax pick with the following results. For comparison the base sheet was also sized with water alone (no starch) and similarly tested. The data is summarized below in Table C.

Table C

| | Size Pickup % | Burst (Mullen)[1] (No./sq.in.) | (Gurley)[2] (sec./300 ml) | Dennison Wax Pick[3] Wire Side | Felt Side |
|---|---|---|---|---|---|
| Continuous | 5.7 | 19.0 | 107.8 | 17.0 | 9.0 |
| Conventional | 6.3 | 19.2 | 110.7 | 16.0 | 9.5 |
| Water only | 0 | 11 | 17 | 3.0 | 3.0 |

[1]Tappi Standards & Suggested Methods No. T-403
[2]Tappi Standards & Suggested Methods No. T-460
[3]Tappi Standards & Suggested Methods No. T-459

The data indicates that as a paper size the non-uniform size prepared by the subject continuous enzyme conversion process is as effective as a size uniformly enzyme-converted by the conventional batch process.

I claim:

1. Method for continuous preparation of cooked thinned starch paste ready for application as a starch size or starch adhesive, comprising in combination the steps of:

a. continuously introducing a feed into a single chamber converting zone provided with agitation means, said feed consisting essentially of a water slurry of raw granule starch containing from 10 to 45% by weight starch on a dry solids basis;

b. also continuously introducing into said chamber a starch thinning enzyme consisting essentially of alpha amylase;

c. maintaining in said converting zone for an average residence time of five minutes or longer a continuously agitated and substantially uniformly mixed body of starch suspended in water containing said alpha amylase in active condition for thinning said starch said aggitation causing continual backmixing from the lower to the upper portion of said zone, said body being at a temperature which is above the gelatinization temperature of the starch to gelatinize the incoming granule starch and at which said alpha amylase is active, and to subject the gelatinized starch, consisting of a blend of starch molecules of different degrees of enzyme conversion, to further enzyme conversion for viscosity reduction, said body of starch being maintained at a predetermined substantially uniform viscosity of not over 5000 centipoises, as determined by a Brookfield Viscometer at 100 rpm and 190° F., and having a reducing sugar content corresponding to a dextrose equivalent (D.E.) of below 3%;

d. continuously withdrawing from said chamber, in proportion to the volume of said feed, a stream of completely gelatinized thinned starch paste consisting of said blend of starch molecules of different degrees of enzyme conversion at substantially the same viscosity and D.E. as the body of starch maintained in said chamber; and e. inactivating the alpha amylase enzyme in said withdrawn paste without substantial further enzyme conversion of said withdrawn paste.

2. The method of claim 1 in which said feed slurry contains at least 15% by weight starch on a dry solids basis.

3. The method of claim 1 in which said withdrawn paste has been maintained in said converting zone for an average residence time of from 5 to 60 minutes.

4. The method of claim 1 in which said alpha amylase is a bacterial alpha amylase and said body of starch within said converting zone is maintained at a temperature of from 180° to 200° F.

5. The method of claim 1 in which said withdrawn paste has been maintained in said converting zone for an average residence time of at least 10 minutes.

6. Method for continuous preparation of cooked thinned starch paste ready for application as a starch size or starch adhesive, comprising in combination the steps of:

a. continuously introducing a feed into a single chamber converting zone provided with agitation means, said feed consisting essentially of a water slurry of raw granule starch containing from 15 to 40% by weight starch on a dry solids basis;

b. also continuously introducing into said chamber a starch thinning enzyme consisting essentially of a bacterial alpha amylase;

maintaining in said converting zone a continuously agitated and substantially uniformly mixed body of starch suspended in water containing said alpha amylase in active condition for thinning said starch said agitation causing continual backmixing from the lower to the upper portion of said zone, said body being at a temperature of from 180° to 200° F. to gelatinize the incoming granule starch and to subject the gelatinized starch, consisting of a blend of starch molecules of different degrees of enzyme conversion to further enzyme conversion for viscosity reduction;

d. continuously withdrawing from said chamber, in proportion to the volume of said feed, a stream of completely gelatinized thinned starch paste consisting of said blend of starch molecules of different degrees of enzyme conversion, said withdrawn paste having been maintained in said converting zone for an average residence time of from 10 to 60 minutes and the conversion thereof having been limited to produce a reducing sugar content corresponding to a dextrose equivalent (D.E.) of below 3%; and e. inactivating the alpha amylase enzyme in said withdrawn paste without substantial further enzyme conversion of said withdrawn paste.

* * * * *

UNITED STATES PATENT AND TRADEMARK OFFICE
CERTIFICATE OF CORRECTION

PATENT NO. : 4,014,743

DATED : March 29, 1977

INVENTOR(S) : William C. Black

It is certified that error appears in the above–identified patent and that said Letters Patent are hereby corrected as shown below:

Col. 10, line 31 add c. prior to "maintaining".

Signed and Sealed this

*twelfth* Day of *July 1977*

[SEAL]

*Attest:*

RUTH C. MASON
*Attesting Officer*

C. MARSHALL DANN
*Commissioner of Patents and Trademarks*